United States Patent [19]

Whiteside et al.

[11] Patent Number: 5,002,545
[45] Date of Patent: Mar. 26, 1991

[54] TIBIAL SURFACE SHAPING GUIDE FOR KNEE IMPLANTS

[75] Inventors: Leo A. Whiteside, Bridgeton, Mo.; Carl M. Stamp, Cordova, Tenn.

[73] Assignee: Dow Corning Wright Corporation, Arlington, Tenn.

[21] Appl. No.: 303,709

[22] Filed: Jan. 30, 1989

[51] Int. Cl.⁵ .............................................. A61F 5/04
[52] U.S. Cl. ...................................... 606/80; 606/86; 606/88; 606/89
[58] Field of Search ....................... 606/79, 80, 81, 84, 606/85, 86, 87, 88, 96, 98, 89

[56] References Cited

U.S. PATENT DOCUMENTS

| | | | |
|---|---|---|---|
| 4,103,683 | 8/1978 | Neufeld | 606/96X |
| 4,421,112 | 12/1983 | Mains et al. | 606/88 |
| 4,467,801 | 8/1984 | Whiteside | 606/88 |
| 4,474,177 | 10/1984 | Whiteside | 606/88 |
| 4,736,737 | 4/1988 | Fargie et al. | 606/88 |
| 4,738,253 | 4/1988 | Buechel et al. | 606/96 X |
| 4,773,407 | 9/1988 | Petersen | 606/88 |

OTHER PUBLICATIONS

Dow Corning Wright document entitled: "Brief Surgical Procedure for the Whiteside Ortholoc II TM Posterior Stablized Knee System" published prior to 01/30/89.

Primary Examiner—Robert A. Hafer
Assistant Examiner—Kerry Owens
Attorney, Agent, or Firm—Howard W. Hermann

[57] ABSTRACT

The present invention provides a shaping guide to permit accurate shaping of the tibial plateau while saving the anterior cruciate ligament. An alignment rod is located anterior to the anterior cruciate ligament and along the anterior cortex of the intermedullary canal of the tibia provides points of reference for all shaping operations. The shaping guide of the present invention is adjustable with respect to the handle portion of the rod so that the amount of resection of the tibial plateau can be controlled readily by the surgeon by raising or lowering of the cutting guide surfaces for resection of the tibia.

6 Claims, 3 Drawing Sheets

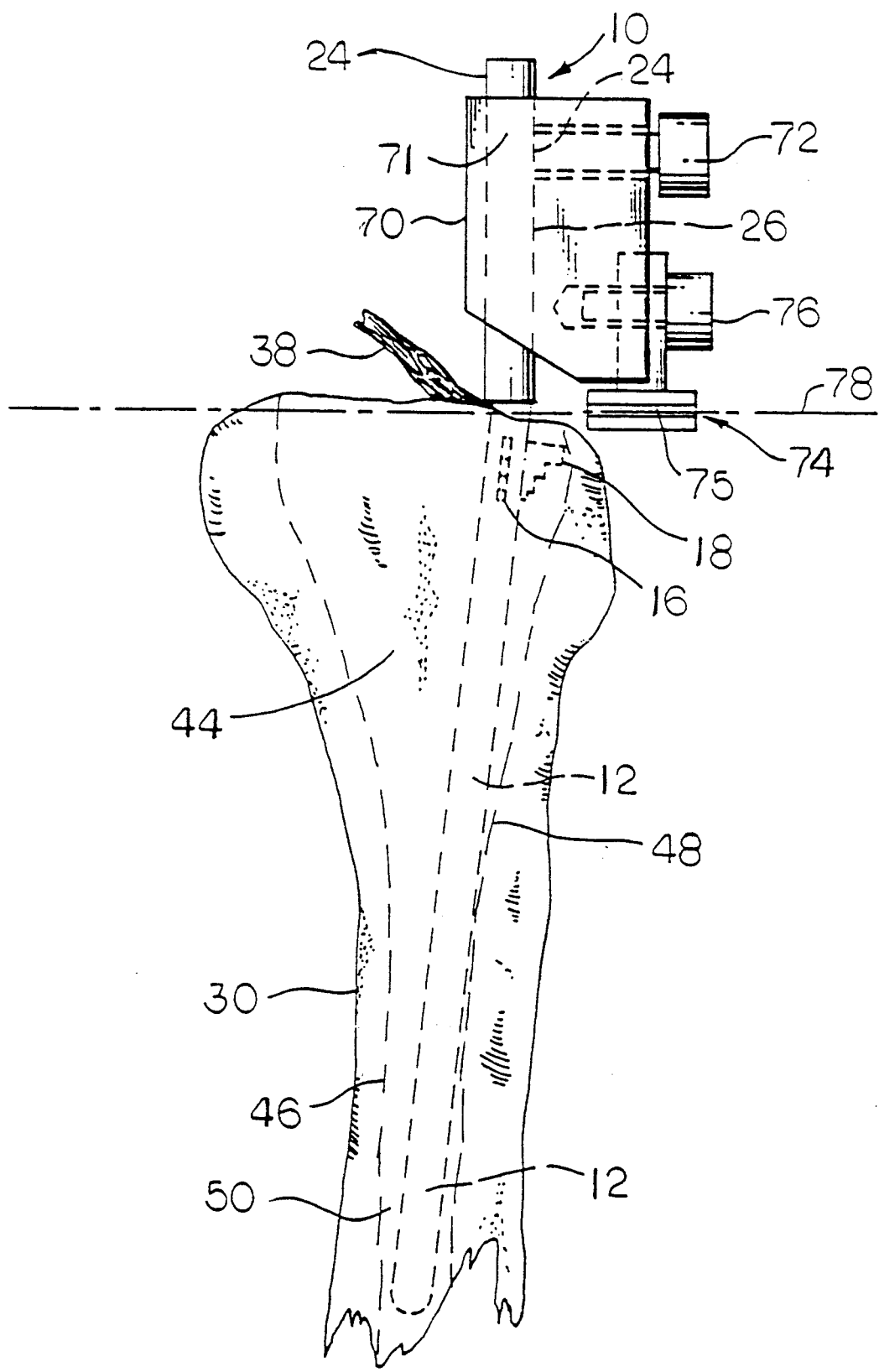

TIBIAL SURFACE SHAPING GUIDE FOR KNEE IMPLANTS

BACKGROUND OF THE INVENTION

This invention relates to a method and apparatus for shaping the proximal surface of a human tibia, employing a novel adjustable shaping guide, which enables resection to be accomplished without sacrifice of the anterior cruciate ligament.

In replacing a knee joint which has been damaged due to disease or trauma, it is very important that the prosthesis used to replace the damaged portion of the joint be properly aligned with respect to the bone to which the prosthesis is fixed. Particular problems are encountered when resection of the proximal surface of the tibia is required, in that most shaping instrumentation requires sacrifice of the anterior cruciate whereas in most replacements the stability of the knee with replacement implants in place would be significantly improved by retaining the ligament.

To enable a surgeon to shape the proximal tibia to receive a tibial component of a total knee joint prosthesis, Leo A. Whiteside, one of the named inventors herein, developed a method and apparatus for shaping a proximal tibial surface which is claimed in U.S. Pat. No. 4,467,801. That patent teaches the use of an intramedullary alignment guide which provides the surgeon with a means for determining the central long axis of the tibia and a means by which the surgeon can shape the proximal tibia relative to that axis by attaching a planer or similar shaping instrument to that alignment guide. The anterior cruciate ligament is generally sacrificed using that method and apparatus.

SUMMARY OF THE INVENTION

It is a primary object of this invention to provide a method and means for aligning a shaping guide which overcomes the problems heretofore experienced in connection with resection of the tibia for implantation of a prosthesis while sparing the anterior cruciate ligament. The method and apparatus of this invention provide for simple, but accurate shaping guide alignment. Another object of the present invention is to provide a tibial shaping guide which is designed to be fixed to support means present on (e.g., the handle of) an alignment guide so that shaping can be done relative to the guide. A principal object is to provide an improved means for alignment of the guide vertically and in the anterior/posterior direction, providing a surgeon with a shaping guide which has a main body that is attached and aligned easily during the surgical procedure. It is another object of the present invention to provide a shaping guide which is vertically adjustable and which provides for alignment to permit accurate shaping of the tibial plateau. Such alignment coupled with attachment to a rod located along the anterior cortex of the intermedullary canal of the tibia provides points of reference for all shaping operations.

The shaping guide of the present invention is adjustable with respect to the handle of the alignment guide so that the amount of resection of the tibial plateau can be controlled readily by the surgeon by raising or lowering of the cutting guide surfaces. The cutting guide body which attaches to the handle of the alignment guide, remains fixed to the handle after the guide body is adjusted. The cutting guide body contains at least one shaping guide surface for resection of the tibia which is formed as a part of the cutting guide body.

Briefly summarized, the invention contemplates the use of a rod which is inserted into the intermedullary canal of the tibia from a point anterior to the anterior cruciate ligament and extending along the anterior cortex of the intermedullary canal of the tibia, preferably through the isthmus of the canal and a short distance beyond the isthmus into the widening part of the canal below the isthmus. A guide rod having a length of about 10 inches is generally required for this purpose.

BRIEF DESCRIPTION OF THE DRAWINGS

The above and other objects, features, and advantages of the present invention will become apparent to those skilled in the art upon an examination of the following description and drawings which are illustrative of the present invention. In the Drawings.

DETAILED DESCRIPTION OF THE INVENTION

Figure 1:
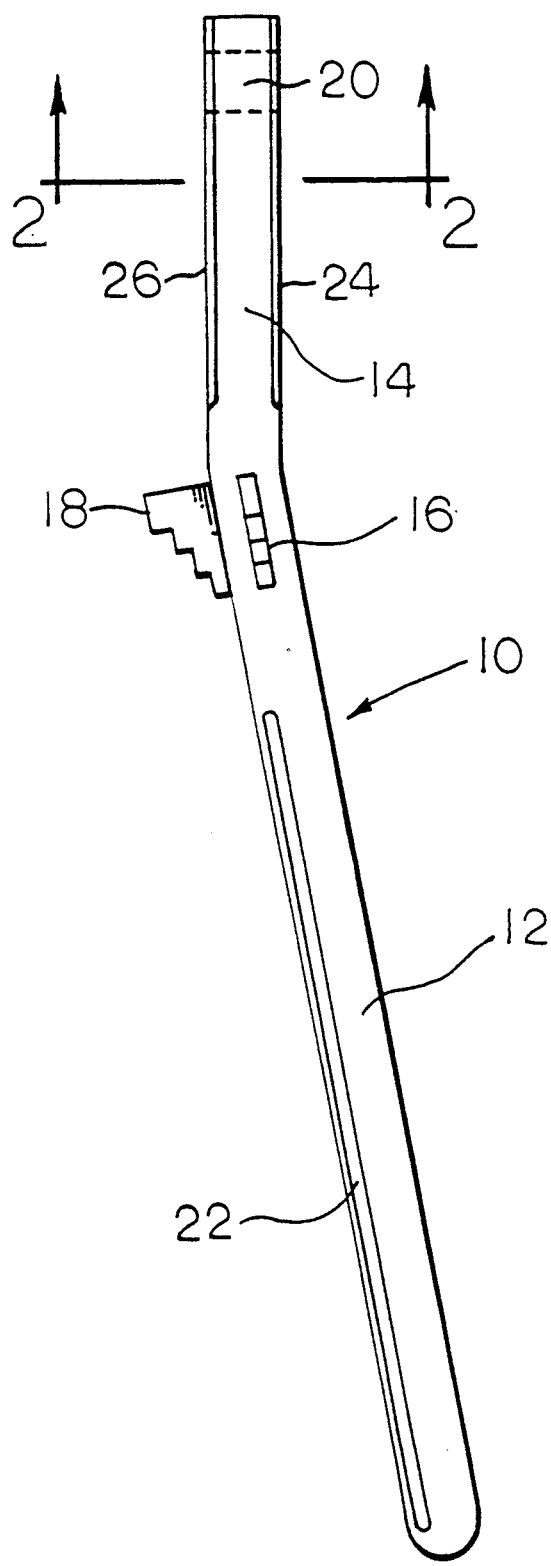
FIG. 1 is a side view of a guide rod of the present invention.
Figure 2:
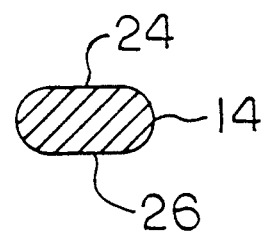
FIG. 2 is a crossectional view along Line 2—2 of FIG. 1.

Referring to the Drawings, and specifically to FIG. 1, there is seen an intramedullary alignment guide 10 having a rod portion 12 adapted to be positioned in the intramedullary canal of a tibia. Guide 10 has a guide handle portion 14 attached to and set at a pre-selected angle with respect to the axis of the intramedullary rod portion 12. Locking fins 16 and 18 are provided for anchoring the rod at a selected orientation within the intramedullary canal. Generally a third locking fin would be positioned on the side of the rod opposite of fin 16.

Figure 3:
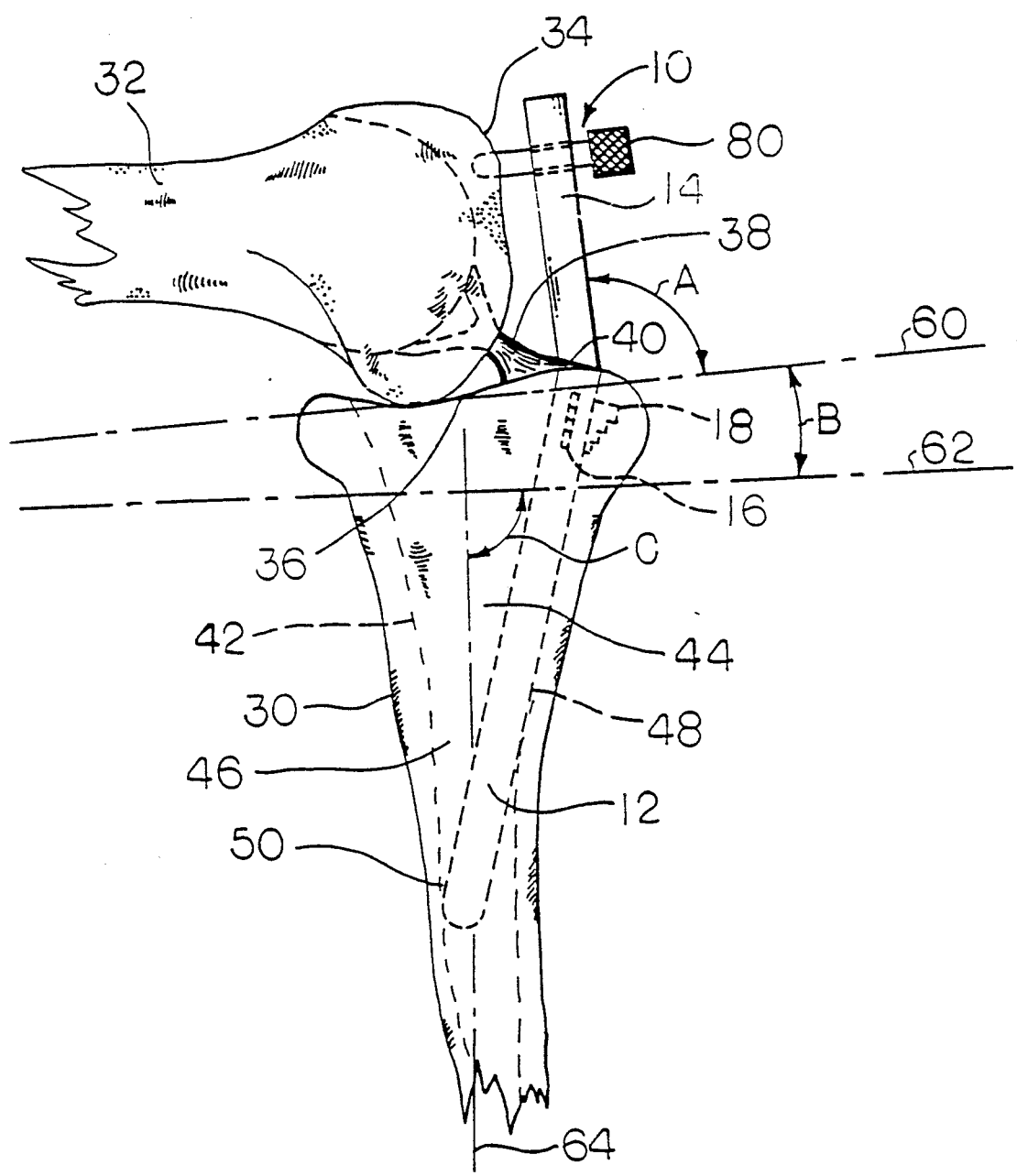
FIG. 3 is a side perspective view showing an alignment guide inserted into the intramedullary canal of a tibia (with parts broken away), and, FIG. 4 is a side perspective view showing a cutting guide block attached to an alignment guide of this invention.

A circular bore 20 is provided through the handle portion to assist the surgeon in rotating the rod during insertion, if necessary, and for removing the alignment rod from the bone after use. Optional flutes or indentations may be provided on the stem of the rod as indicated at 22. Flattened portions on the handle 24 and 26 are provided in order to allow placement on the handle of a cutting guide block 70 which is thereby prevented from rotation on the handle. The flattened sides may be oriented as desired. It will also be apparent to one skilled in the art that rotation could be prevented by one flattened surface or a combination of grooves or keys. In FIG. 3 there is shown a knee joint having a femur 32 which has a distal condylar surface 34, and a tibia 30 which has a proximal tibial plateau 36. Cruciate ligament 38 joins tibia 30 to femur 32. The tibia comprises exterior hard cortical bone 42 and interior soft cancelous bone in the intramedullary canal 44. The posterior cortex joining the cortical and cancelous bone is indicated by numeral 46 and there is a similar cortex 48 along the anterior surface of the intramedullary canal.

As also seen in FIG. 3, rod 12 extends through an opening 40 which is made anterior to cruciate ligament 38 and extends down the intramedullary canal along cortex 48 somewhat beyond isthmus 50 which is the narrowest part of the intermedullary canal. Fin 16 and 18 serve to prevent rotation and to stabilize the alignment device.

It is desirable that the handle portion 14 of alignment guide 10 be designed so that angle A between the axis of the handle portion 14 and line 60, which represents the plane of the tibial plateau surface, is 90 degrees. Angle B indicates the degree of tilt between tibial plateau 36 and line 62 which is perpendicular to axis 64 of the tibia as indicated by angle C. In order for the surgeon to obtain proper alignment it is necessary to provide him with a series of rods 10 having an angle between the axis of the rod portion 12 and handle portion 14 varying between about 9 degrees and 12 degrees to take into account individual differences in the shape of the tibia. The proper angle is generally determined by the surgeon using X-rays during the course of pre-operative planning.

As shown in FIG. 4, a cutting guide block 70 which contains an opening 71 adapted to slidable fit over the handle portion 14 is adjustably secured in place by means of a threaded set screw 72 which engages a flattened surface 26 of the handle. Other adjustable securing means can be substituted by those skilled in the art. Carried by cutting guide block 70 is a guide means 74 which contains a slot 75 for guiding a resection tool. Guide means 74 is adjustable secured to block 70, preferably by means of a set screw 76. Guide means 74 may thus be raised or lowered to set slot 75 on the desired line of resection 78.

The manner in which the method of the present invention may be carried out will now be described. The preoperative procedures for radiographically determining the central long axis of the tibia and the angle at which resection of the proximal tibia plateau surface is to be made with respect to that axis is the same as is typically employed in other methods known to surgeons skilled in the art. As noted above, the angle B of inclination between the tibial plateau and a line perpendicular to the axis of the tibia is determined. The entry point 40 for the intramedullary reamer is identified. Operatively, the usual surgical approach is made after the interior aspect of the knee is exposed. The knee is flexed, generally to 100 degrees, so that the surfaces of the femur and tibia can be visualized. The preferred alignment guide as a rod portion with a diameter of 0.370 inches (9.4 mm) and a suitable drill bit is selected by the surgeon to accommodate such diameter rod. The drill is advanced along the cortical surface 48 thereby removing soft cancellous bone from the intramedullary canal. A reamer may be used in forming the opening for rod portion 12. The opening should be extended through the isthmus of the tibia.

Following preparation of the tibia for the alignment guide 10, the guide is inserted into the tibia to a location where the fins almost touch the proximal surface. A small diameter pin 80 is then inserted into hole 20 on guide 10. Using pin 80 as a guide, rotational alignment is set by aligning the pin with the intracondylar notch of femur 32. The alignment guide is then driven into place, with fins 16 and 18 engaging the proximal surface of the tibia.

The cutting guide body, intramedullary alignment guide, shaping means guide, and associated components are all preferably manufactured from a suitable surgical grade of stainless steel or other metal commonly employed by those skilled in the art to construct surgical tools for use in contact with the body. The exact composition of the materials used to construct the above forms no part of the present invention as long as it performs the desired function; other materials suitable for use within the body and for the intended uses of the above may be used without altering the nature of the invention.

The manner in which the apparatus of the present invention may be used will now be described. The present invention relies on the use of an intramedullary alignment guide. The intramedullary alignment guide 10 has been inserted within the bore in tibia 30 up to the point where fins almost touch the proximal surface of tibia 30. The rotational alignment of guide handle 14 is adjusted and guide rod 12 is then driven into the tibia using a mallet on the impactor until the fins 16 and 18 are embedded in the cortical bone of the tibia. The cutting guide block 70 is then secured in the desired position on the handle portion 14. The depth of the resection is then adjusted by raising or lowering guide 74 and tightening set screw 76.

Thereafter the surgeon is able to shape the tibial plateau in accordance with conventional surgical procedures using the cutting guides 75. As will be appreciated, severance of the ligament 38 and the bony island to which it is attached is not required using the apparatus and method of this invention.

After aligning main body 70 relative to the tibial plateau, a conventional shaping means such as an oscillating saw or a hand saw (not shown) is then introduced into guide slot 75 to enable the surgeon to resect the plateau accurately along the plane indicated by line 78. The cuts are designed to fit the particular prosthesis to be fixed to the proximal tibia. The prosthesis is affixed to the tibia in conventional fashion using appropriate pins, posts or fins, which may be integral with the prosthesis, depending on the particular design. The surgeon can cut such holes or slots as are deemed desirable for securing a particular prosthesis. Appropriate slots or holes can be provided in a suitable guide block also attachable to handle 14 to assist in such cutting procedures. When shaping is completed, the intramedullary alignment guide is removed and the prosthesis installed in accordance with conventional techniques.

Other modifications of the apparatus and method of the present invention will become apparent to those skilled in the art from an examination of the above specification and drawings. Therefore, other variations of the present invention may be made which fall within the scope of the following Claims even though such variations were not specifically discussed above.

That which is claimed is:

1. An alignment guide having an intramedullary alignment rod portion which is fixed within the intramedullary canal of a tibia comprising:
   (A) a rod portion adapted to be positioned in the tibial intermedullary canal in such a manner as to have the rod portion enter the intermedullary canal at a point anterior to the anterior cruciate ligament and to have the central long axis of the rod positioned adjacent and parallel to the anterior cortex of the intermedullary canal,
   (B) an offset handle portion of noncircular crossection integral with said rod portion, the angle between said rod portion and said offset portion being between about 9° and 12° and being such that said handle is perpendicular to the plane of the tibia plateau when the rod portion is in place,
   (C) a cutting guide body having an opening adapted to fit over said handle portion, said guide body, (D) means for adjustably fixing said cutting guide body in proper alignment with respect to the tibial plateau, (E) at least one tibial plateau surface shaping guide carried by said guide body having shaping guide surfaces thereon to permit at least one shaping step in the resection of the proximal tibia in such a manner that the anterior cruciate ligament is not cut and a preselected tibial knee prosthesis can be attached to the shaped proximal tibia, said cutting guide body remaining fixed to the intramedullary alignment guide handle during the shaping process.

2. The shaping guide as claimed in claim 1 wherein the shaping means guide surface is adjustable vertically relative to said cutting guide body.

3. The shaping guide as claimed in claim 2 wherein said rod portion is adapted to extend through the isthmus of said intermedullary canal.

4. The shaping guide as claimed in claim 1 wherein the means for adjustable attachment comprises a threaded set screw which engages a flattened side of said handle portion of said intramedullary rod.

5. A proximal tibial surface shaping guide for fixation to an intramedullary alignment guide having (a) an intramedullary alignment rod portion which is fixed within the intramedullary canal of a tibia in such a manner as to have the central long axis of the rod adjacent to the parallel with the anterior cortex of the intramedullary canal of said tibia, said rod portion extending through the isthmus of said tibia, and (b) a handle portion integral with said rod portion and offset therefrom at an angle of about 9° to 12°, said handle portion having on the anterior side thereof, a flattened surface, (c) a shaping guide body having an opening therethrough slidably fitted over said handle portion, a threaded set screw threaded through said body and adapted to be tightened against said flattened handle portion to permit vertical adjustment of said guide body on said handle portion, and (d) a tibial surface shaping guide, vertically adjustable, carried by said cutting guide body.

6. A method of preparing a human tibia having a proximal tibial plateau surface and an intramedullary canal located at the center of a tubular shaft of hard compact cortical bone, said canal being filled with a softer cancellous bone, comprising;

(a) boring an opening in said surface at a point anterior to the anterior cruciate ligament of the tibia and along the anterior cortical surface of the intramedullary canal of the tibia in such a manner as to have the central long axis of the opening adjacent to and parallel with said cortical surface of the tibia and extending through the isthmus of said tibia, (b) inserting into said opening a rod portion of an intramedullary alignment guide which rod portion extends through the isthmus of said tibia, and has integral therewith a handle portion and offset therefrom at an angle of about 9° to 12°, said handle portion having at least one flattened surface, (c) installing over said handle portion a shaping guide body having an opening therethrough slidably fitted over said handle portion, (d) affixing said body at a desired location on said handle by means of a threaded set screw threaded through said body and tightened against said flattened handle portion adjusting a tibial surface shaping guide adjustably carried by said cutting guide body, and, (e) performing resection of the plateau of said tibia using said shaping guide as a means to determine the location and shape of such resection.

* * * * *